United States Patent
Faupel

(10) Patent No.: US 8,712,515 B2
(45) Date of Patent: Apr. 29, 2014

(54) METHOD AND APPARATUS FOR DISEASE DIAGNOSIS AND SCREENING USING EXTREMELY LOW FREQUENCY ELECTROMAGNETIC FIELDS

(76) Inventor: Mark L. Faupel, Alpharetta, GA (US)

( * ) Notice: Subject to any disclaimer, the term of this patent is extended or adjusted under 35 U.S.C. 154(b) by 1151 days.

(21) Appl. No.: 12/540,554

(22) Filed: Aug. 13, 2009

(65) Prior Publication Data

US 2010/0049078 A1 Feb. 25, 2010

Related U.S. Application Data

(60) Provisional application No. 61/111,567, filed on Nov. 5, 2008, provisional application No. 61/091,100, filed on Aug. 22, 2008.

(51) Int. Cl.
*A61B 5/04* (2006.01)
*A61B 5/05* (2006.01)
*A61B 10/00* (2006.01)

(52) U.S. Cl.
USPC ........... 600/547; 600/372; 600/393; 600/407; 600/551

(58) Field of Classification Search
USPC ............ 600/372, 393, 407, 547, 551; 606/32; 607/59, 62
See application file for complete search history.

(56) References Cited

U.S. PATENT DOCUMENTS

| | | | |
|---|---|---|---|
| 4,328,809 A | 5/1982 | Hirschowitz et al. | |
| 4,407,300 A | 10/1983 | Davis | |
| 4,416,288 A | 11/1983 | Freeman | |
| 4,486,835 A | 12/1984 | Bai et al. | |
| 4,557,273 A | 12/1985 | Stoller et al. | |
| 4,955,383 A | 9/1990 | Faupel | |
| 6,022,316 A * | 2/2000 | Eppstein et al. | 600/309 |
| 7,194,306 B1 * | 3/2007 | Turcott | 607/17 |
| 8,262,575 B2 * | 9/2012 | Davies | 600/442 |
| 2003/0028221 A1 * | 2/2003 | Zhu et al. | 607/9 |
| 2003/0204148 A1 | 10/2003 | Lange et al. | |
| 2003/0216661 A1 | 11/2003 | Davies | |
| 2006/0100488 A1 | 5/2006 | Davies | |

FOREIGN PATENT DOCUMENTS

| | | |
|---|---|---|
| EP | 1238630 | 5/1982 |
| JP | H11-50333 | 2/1999 |
| JP | 2003-116802 A | 4/2003 |
| JP | 2005-525900 A1 | 9/2005 |
| RU | 2159574 C1 | 11/2000 |
| RU | 2189172 C2 | 9/2002 |

OTHER PUBLICATIONS

PCT International Search Report and Written Opinion for PCT/US2009/053669; Nov. 25, 2009.
Eurasian Search Report dated Sep. 7, 2011 for Eurasian Patent Application No. 201170365.

* cited by examiner

*Primary Examiner* — Sean Dougherty
*Assistant Examiner* — Devin Henson
(74) *Attorney, Agent, or Firm* — Pepper Hamilton LLP

(57) ABSTRACT

Novel methods and apparatus for diagnosing or screening disease states in living organisms by the measurement and analysis of extremely low frequency electromagnetic fields, particularly extremely low frequency alternating current. The measurement of such fields is performed at a single point or at several test points on or in the body and compared to one or more reference. Information in the time-varying electromagnetic field is collected, then processed by diagnostic or screening algorithms to provide information about the disease state of the tissue being assessed.

28 Claims, 6 Drawing Sheets

METHOD AND APPARATUS FOR DISEASE DIAGNOSIS AND SCREENING USING EXTREMELY LOW FREQUENCY ELECTROMAGNETIC FIELDS

This application claims benefit of priority to U.S. provisional patent application No. 61/111,567 filed Nov. 5, 2008 and U.S. provisional patent application No. 61/091,100 filed Aug. 22, 2008, each of which is hereby incorporated by reference in its entirety.

TECHNICAL FIELD

Disclosed is a novel method and apparatus for diagnosing or screening disease states in living organisms by the measurement and analysis of extremely low frequency electromagnetic fields. The measurement of such fields is performed at a single point or at several test points on or in the body and compared to one or more reference. Information in the time-varying electromagnetic field is collected, then processed by diagnostic or screening algorithms to provide information about the disease state of the tissue being assessed.

BACKGROUND

It is well accepted that the biological activity of organisms, organ systems and cells produces measurable electromagnetic activity. At one end of the spectrum is the high frequency activity (alternating current) of neural tissue and at the other end is the steady state (direct current) activity hypothesized to indicate abnormal cell or tissue growth. For example, medical applications of high frequency (AC) electromagnetic field measurements are manifest in electroencephalographic and electrocardiographic devices. More recently, direct current (DC) fields have been studied as a method of cancer diagnosis. For example, U.S. Pat. No. 4,328,809 to B. H. Hirschowitz and U.S. Pat. No. 4,955,383 to M. L. Faupel contemplate devices and methods for measuring and analyzing DC electropotentials for disease diagnosis or screening. In these inventions, information in the extremely low frequency alternating current (AC) band is filtered out through averaging a multiplicity of signals taken over time. Higher frequency information is filtered out using active or passive digital or analog filters. Other manifestations of this approach have been articulated in U.S. Pat. No. 4,407,300 to Davis and U.S. Pat. No. 4,557,273 to Stoller et al. Davis, for example, discloses the diagnosis of cancer by measuring the electromotive forces generated between two electrodes applied to a subject.

If measurements are taken from several test points on the body, as contemplated in the aforementioned Hirschowitz and Faupel patents, as well as in U.S. Pat. No. 4,416,288 to Freeman and U.S. Pat. No. 4,486,835 to Bai, comparisons of the averaged DC potentials from the plurality of test points may be of particular interest. Furthermore, the averaged DC voltages may be further analyzed by discriminant function analysis, as disclosed in particular by the aforementioned Faupel patent.

These disease diagnosis techniques using only DC electropotentials sacrifice information (e.g., low frequency AC information) for ease of processing afforded by a singular filtered and/or averaged measurement from each test site on the body. Unfortunately, this loss of information may compromise diagnostic accuracy of many disease states. For example, public disclosure of clinical studies involving analysis of DC potentials indicate that while there may be some degree of diagnostic accuracy for large (palpable) cancers, the same approach appears to be relatively ineffective for small (nonpalpable) cancers. Since it is well recognized that early detection of disease states offers the best chance for patient survival, improvement in this capacity over previous disclosures is indicated. Moreover, previous pattern recognition techniques used for analysis of electropotential fields may be overly simplistic in that they do not take into account the complexities of biological systems and their disease states. To this point, it is known that the biology and concomitant electromagnetic activity of malignant tumors, for example, change over time. In order to maximize effectiveness, novel diagnostic and screening techniques based on the measurement of electromagnetic fields must take into account both the short term changes in electrical activity (e.g., extremely low frequency AC fields) as well as the longer term changes which occur as a disease state progresses. Failure to do so results in major deficiencies leading to diagnostic inaccuracy.

For example, changes in extremely low frequency alternating current (ELFAC) may differ for malignant vs. benign tumors, because the gating mechanisms controlling ion transport across the epithelial tissue layer can differ between the diseased and nondiseased condition, or other reasons. It is known that malignant epithelial cells lose, to varying degrees, the ability to transport ions and fluids across the epithelial layer. It is this low frequency time-varying phenomena which is lost by restricting analysis of electrical signals to an averaged and/or filtered DC component.

In addition, changes over the longer term indicate that the electromagnetic behavior of small malignant tumors may be very different from that of larger tumors, which have been found to produce redox potentials as a result of the degradation of tissue within the core of the tumor. Another factor is smaller tumors may be more metabolically active and therefore more relatively depolarized than larger tumors.

It follows then that analysis of important electromagnetic changes must take these factors into account in order to maximize diagnosis and screening of disease states.

SUMMARY

Disclosed is a novel and improved method and apparatus for integrating electromagnetic information over time in the form of a set of novel pattern recognition outputs for the diagnosis and screening of disease states. The important diagnostic inputs to pattern recognition are referred to here as extremely low frequency alternating currents (ELFACs). Such method and apparatus operate to measure and analyze electromagnetic activity from regions of diseased tissue on or internal to a living organism.

Further disclosed is a novel and improved method and apparatus for pattern recognition which takes into account the biological changes which occur as a disease state progresses. This is accomplished by integrating non-electromagnetic information (e.g., size or area of diseased tissue as indicated by an imaging study or palpation of a tumor) with the electromagnetic information.

Further disclosed is a novel means for identifying and discriminating diagnostically important ELFAC activity from electromagnetic activity due to noise at the interface between the organic tissue and the measurement apparatus. This is accomplished by constant measurement of ELFAC activity from the point a measurable signal is achieved from the organism but recording and analyzing only the portion of the signal indicating that ELFAC activity has achieved a noise-minimized and therefore diagnostically useful state. Since this is expected to vary on a subject by subject basis, a novel means of determining noise minimized performance using pattern recognition is disclosed by the present invention.

In some embodiments, the invention provides a novel and improved method and apparatus for screening an organ system of a living organism for a disease condition. In some embodiments, noise-minimized ELFACs are recorded from several locations involving an organ system such as the prostate gland or breast. The resultant information is analyzed using nonlinear pattern recognition techniques to determine if a disease state exists in an organ system for which no other disease related symptoms are observable. Improvement in screening accuracy may be achieved by integrating subject variables such as chronologic age or organ characteristic (e.g., size) information along with ELFAC data into the screening pattern recognition program.

Still further embodiments of the present invention provide a novel and improved method for ELFAC diagnosis of malignant disease states. In this embodiment, recordings of noise-minimized ELFACs from locations on and near tissue suspected of harboring malignant activity are analyzed using specific nonlinear pattern recognition programs which incorporate ELFAC data with known symptomatology of the suspect tissue, such as tumor size, level of suspicion from imaging studies, age of subject, etc. The goal of this approach is to take advantage of the interaction between progressive biological changes which occur during carcinogenesis, tumor growth, metastasis and their resultant electromagnetic alterations. In situations where bilaterally of the organ system is accessible by the measurement apparatus, as with the breast or extremities, comparison of the suspect breast or extremity with the unaffected or opposite breast or extremity can be used to provide a set of internal control measures. Likewise, a control or reference point can be an external solution of normal saline with any voltage offset calibrated out of the measurement system.

DETAILED DESCRIPTION

Figure 1:
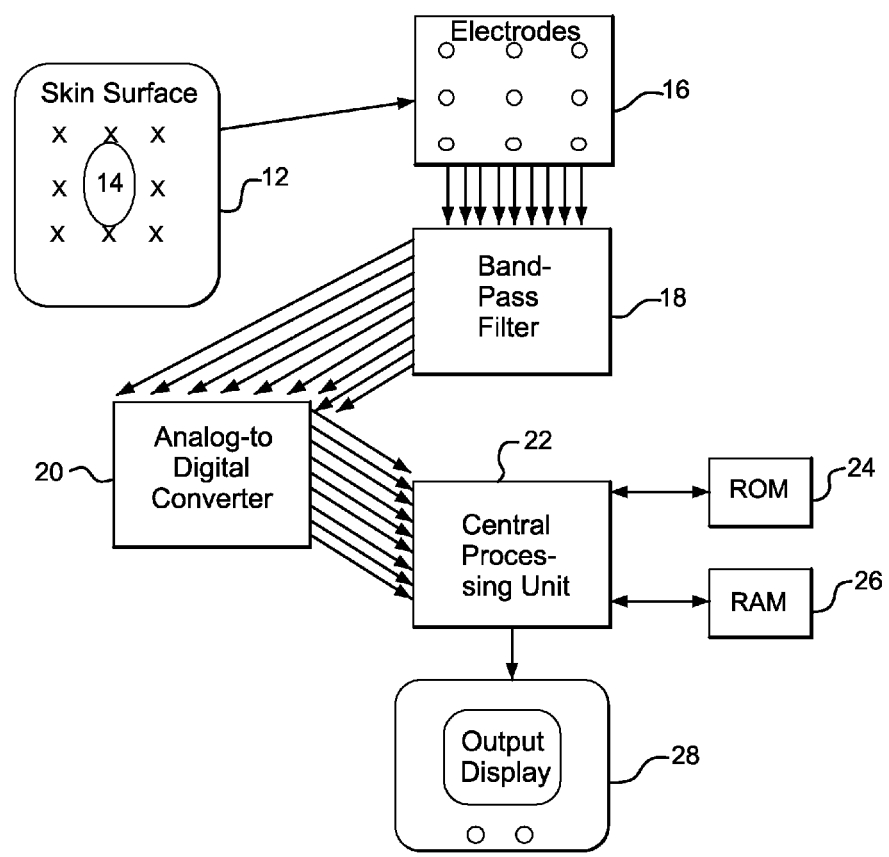
FIG. 1 is a block drawing of the apparatus of some embodiments of the present invention.

The block diagram for the apparatus in accordance with some embodiments of the present invention is disclosed in FIG. 1. The apparatus performs the functions necessary for obtaining and analyzing noise-minimized ELFAC data and integrating those data with other information to produce a disease diagnosis. For the purposes of illustration, the apparatus 10 will be discussed as configured for the diagnosis of skin cancer, although it should be recognized that the method and apparatus can be reconfigured and similarly employed for screening or diagnosing other portions or organs of a living human or animal, such as the mammary gland, prostate gland, colon, lung, naseo-pharynx, or other organ systems.

Figure 2A:
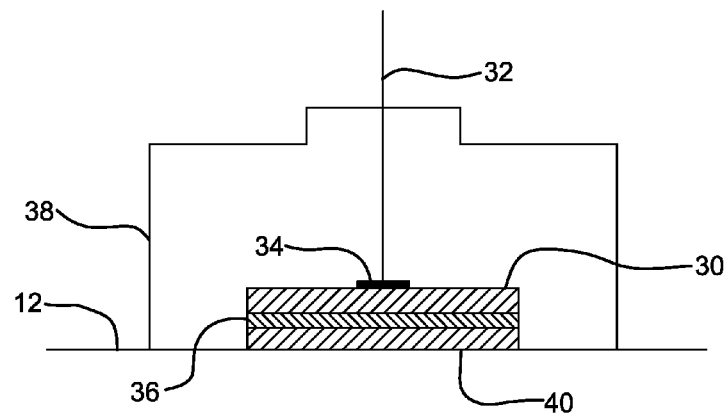
FIGS. 2a and 2b are each a sectional diagram of an electrode for the apparatus of FIG. 1.

In FIG. 1, a human subject's skin surface 12 may have a suspicious lesion 14 visible on the right forearm. Clinical inspection of the lesion may be equivocal and a more certain diagnosis may be needed. In this case, the location of the lesion is known and a multiple sensor array 16 is applied to the area of suspicion and a reference sensor is applied to the mirror image positions on the opposite (left) forearm (not shown). It should be recognized that the opposite forearm is being used as the reference. In other examples, the reference could be a saline solution or other external reference standard, or an undiseased portion of the same organ, or other undiseased tissue of the patient, etc. Assume, however, for the purposes of discussion, that the area of a lesion 14 is not known, as in the case of screening for breast cancer. In this situation, a large array of electrodes 16 would be used to identify any area of suspicion occurring on either breast, as indicated by asymmetries in the ELFAC activities between the two breasts. This illustrates that different embodiments of the device and method of the present invention contemplate the use of a variety of different electrode arrays depending on the specific application, and whether the application is for disease screening or diagnosis. Likewise, the number of recording sensors 16b may differ depending on the specific application. However, in both examples significant disease can be detected using pattern recognition of ELFAC data in conjunction with other clinical information. Once accessed, analog electromagnetic signals are passed through a bandpass filter 18, converted to digital form at analog to digital converter 20, processed at CPU 22 using ROM 24 and RAM 26, and finally displayed at 28. During processing, the measured value(s) are compared to the reference value(s), and adjusted for other characteristics if desired. The result is then compared, in the case of screening activity, to the reference to suggest the likelihood of disease, and in the case of diagnosis to known patterns to suggest the possibility and type of disease. The actual steps describing the invention are subsequently disclosed more specifically in connection with FIGS. 2, 3 and 4.

Figure 2B:
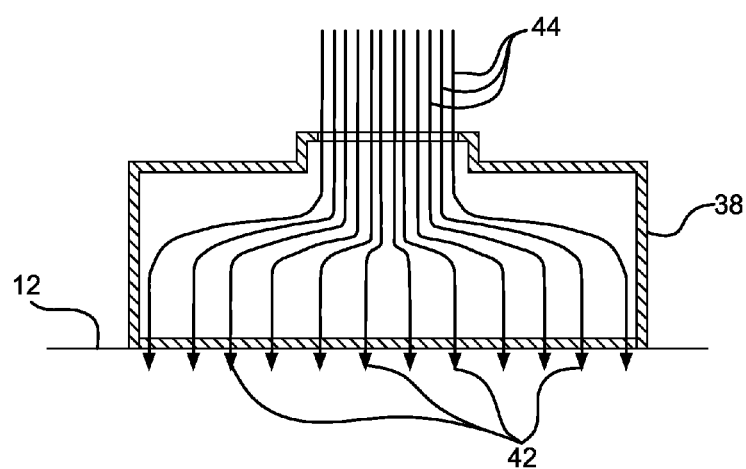

The ELFAC sensing electrodes can be applied either individually or as a set of sensors on an adhesive flexible backing, depending on the application. In both cases, effective spacing of electrodes should be maintained, so that overlap in measurements is minimized. For example, the distance between individual sensors 16b should be at least two times the diameter of the sensor area in contact with the skin or other tissue. If sensors 16b are applied individually, the technician must be trained to position the sensors using the appropriate distances. Ideally, the electrodes 16b should be of a type which do not cause a substantial battery effect due to a dissimilar metals reaction. Most modern electrodes have a solid rather than liquid gel, but the solid gels don't penetrate the stratum corneum, so the signal to noise is not optimal. Another approach is a sensing electrode that consists of a silver or other conductive component 30 having an electrical lead 32 connected to the measurement apparatus 10. This electrical connection is secured to the silver component 30 by a conductive top piece 34. A thin layer of silver chloride 36 is deposited on the surface of the silver component 30. This system is embedded in nonconductive plastic or plastic backing sheets 38. The interface between the organ tissue 12 and the silver chloride surface 36 is mediated by a semi-liquid electrode cream, paste or gel 40 of a known type such as Synapse electrode creme manufactured by Rose Labs, Inc. The primary goal of the electrode cream 40 is to provide a conductive pathway through the electrically resistive corneal layer of the skin 12. Alternatively, the present invention contemplates that the corneal layer of the skin 12 can also be breeched mechanically, either by using recording mini- or micro-electrodes of known types (e.g., Beckman Coulter, Inc. Fullerton Calif.) or by using an array of needle electrodes on a backing sheet which penetrates just beyond the corneal layer of the skin 12 but are of such small diameter not to cause tissue damage. This alternative electrode design is shown in FIG. 2B at 42 and does not require the use of an electroconductive cream, paste or gel 40. In this embodiment, the conductive component 30 contains numerous small penetrating silver or platinum electrodes 42, each of these electrodes could be connected to its own lead which connects to the measurement apparatus 10 or summed to one lead (not shown) connected to measurement apparatus 10.

Alternatively, the stratum corneum, which is responsible for more than 90% of the electrical resistance of the skin, can be removed by controlled use of laser light or a heated wire. In this mode, a laser light in the near infrared range of the electromagnetic spectrum can be concentrated on a thin layer of a dye which absorbs the light energy and dissipates the stratum corneum without penetrating to the dermis below. One or more pores of varying size can be produced in this or any other suitable manner. After the stratum corneum has been selectively compromised in this manner, the electrode is placed over the site and ELFAC potentials measured. In this instance, the electrode 16 or electrodes can be placed directly in the pore or pores thus created, without the need for the electrode cream or gel 40, and without the need for a needle electrode 42.

The measurement device 10 contains multiple recording inputs having electrode leads 32 which are affixed to the subject 12. A reference lead is affixed to the patient in a nondiseased area or alternatively to an external solution of normal saline or other reference standard. Although the example demonstrates the use of a separate reference electrode, each recording electrode could double as a reference electrode for the other electrodes. In this embodiment, each recording electrode except one is scanned relative to the remaining electrode. Next, a different "recording" electrode is automatically selected to be the reference electrode, and so on until each recording electrode has functioned as a reference electrode as well. Since this would result in multiple measurements for each recording electrode, the arithmetic average, median or mode could be taken as representative of each recording channel.

The measurement apparatus 10 can utilize a selective bandpass filter 18, allowing, for example, the analysis of ELFAC signals in the frequency range from 0.001 Hz to 0.1 Hz, preferably 0.01 Hz to 0.1 Hz. Although the present example for cancer diagnosis may utilize signals within this particular frequency range, the present invention also contemplates using bandpass filters sensitive to other low frequency ranges, depending on the type of disease diagnosed or screened for In general, higher ranges may apply to cases where there is higher electrical resistance due to skin for example that must be bypassed to detect breast cancer. Cancers that occur on the linings inside the body such as esophageal lung or cervical don't have this issue and may be closer to true DC (i.e., lower frequency. Until the studies are performed we won't have actual numbers. The bandpass filter 18 may include one or more filters of a known design, as described in the methods for this.

Figure 6:
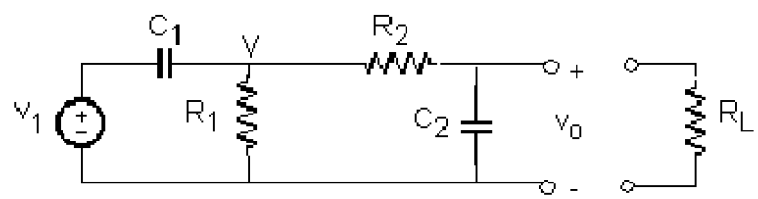
FIG. 6 is a schematic for a passive two-pole band pass filter employed by some embodiments of the invention.

A band pass filter can in principle be constructed by combining a low and high pass filter in cascade. FIG. 6 shows such a filter. The first part ($C_1R_1$) will pass high frequency signals while the second part ($C_2R_2$) will pass the low frequencies (or rejects high frequency signals). However, the filter cannot be considered as a simple cascading of a high and low pass filter since the second part loads the first part. As a result, the overall transfer function is not simply the product of the individual transfer functions of the high and low pass sections.

The above examples of filters are called passive filters since they do not make use of amplifiers. Among the disadvantages of such a filter is that there is no gain and that the load resistor $R_L$ influences the transfer characteristic. A better way to build filters for low to mid-frequency applications is to use operational amplifiers. Such filters are called active filters. The advantage of active filters is that one can provide amplification, and have a filter whose characteristic is independent of the load.

Figure 7:
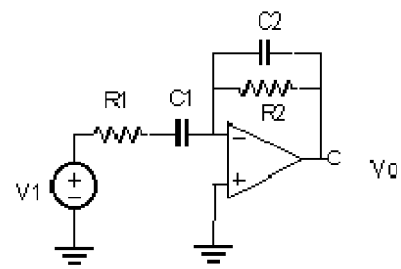
FIG. 7 is a schematic for an active two pole band pass filter employed by some embodiments of the invention.
Figure 8:
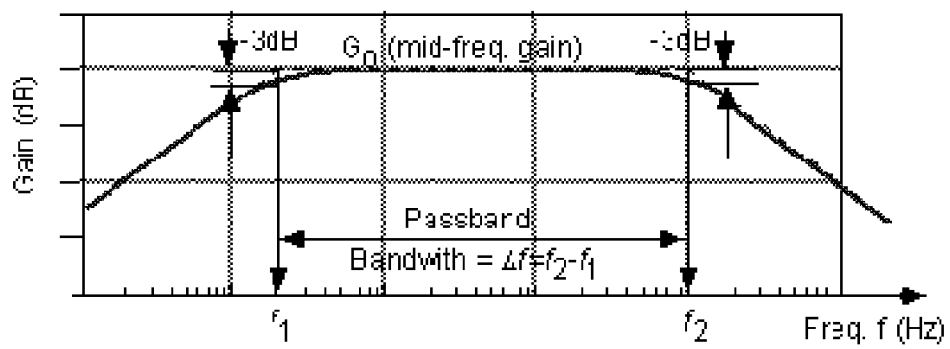
FIG. 8 is a graph depicting the frequency response of a bandpass filter employed in some embodiments of the invention.

A simple active band pass filter (two pole system) is shown in FIG. 7. The frequency response (Bode graph) of the gain is given in FIG. 8.

The band pass filter separately filter the signals on each of the input leads 32 which then pass each of the filtered signals via a separate channel to a multiple input analog-to-digital converter 20. Alternatively, bandpass filtering could occur in the digital domain post analog-to-digital conversion. In addition, the bandpass filter 18 could constitute an individual filtering mechanism for each channel, providing filtering only for that channel with each filtered output connected to the input of the analog-to-digital converter 20.

The analog-to-digital converter 20 ideally should be capable of multiple input multiplexing such as that manufactured by National Semiconductor, Inc. and designated as ADC808. For very large measurement arrays, such as those contemplated for breast cancer screening, more than one multiple input analog-to-digital converter may be necessary, the precise number of converters determined by the channel converters' capacity and the number of channels required for a specific application.

The analog-to-digital converter 20 converts each channel's analog signal to a digital signal which is relayed via a separate output channel to the multiple inputs of a central processing unit 22. The central processing unit is a component of the larger control system which also contains RAM 24 and ROM 26. A stored program in the central processing unit 22 controls signal acquisition and sampling rate, and then processes the digital input data to produce an output to the user regarding the disease state of the tested tissue. Other relevant data such as patient age or size of lesion can be inputted by using a standard computer keypad or touch sensitive screen of conventional type or other input device or method. The central processing unit then integrates this information with the ELFAC data using preprogrammed pattern recognition algorithms. The final output to the user is then fed to a display device 28 such as a computer monitor or printer. The output could also be stored locally or remotely in a network or other memory system. The output can constitute a numerical answer as to the probability of the disease state existing, a yes/no answer as to whether the disease in question exists, or a scalar result indicating the severity of the disease, and/or a false color image, depending on the specific application.

The function and operation of the ELFAC device will be understood from two examples of the steps which embody the basic methodology. The first example summarizes the method for disease screening while the second example characterizes the invention using a diagnostic format.

In the case of screening, the position and disposition of a lesion cannot be identified because the subject is asymptomatic. In this case, a relatively large array of electrodes 16 is positioned either on the surface 12 of the site in question. If the suspected site can be assessed externally through the skin, then the electrodes may be placed on the skin. If more invasive procedures are indicated, the electrodes can be placed internally at the subject organ or site. In the case of breast cancer screening, preferably, the entire surfaces of both breasts would be measured, since the user is unaware if and where a malignancy exists. Once the electrode array 16 is positioned, the reference electrode is placed on an undiseased area of tissue or in a reference standard. Then the ELFAC activity between the reference electrode and each of the measurement electrodes 16 and is immediately measured, bandpass filtered, and processed by a preprogrammed algorithm which determines if and when diagnostically useful ELFAC readings have been obtained from a given test subject. At this point, each individual voltage reading in the waveform is preserved for pattern recognition. This differs from previous techniques in which the apparatus filtered even low frequency AC information by a combination of active filtering and arithmetic averaging of multiple signals taken over time. The approach taken by previous manifestations was to identify only a representative direct current (DC) component by utilizing this selective low pass filtering and signal averaging. Thus any information in the ELFAC component was lost to analysis.

In the case of diagnostic analysis, a sensor 16 is placed at a suspicious site, such as a lesion. The number of electrodes and their positioning will depend, in part, on the size of the suspicious site. Generally, the suspicious site and some surrounding tissue should be analyzed. As with the screening process, a reference electrode is placed at either a reference cite or in a reference standard. A reference site could be a corresponding position on a mirror site (e.g. left arm vs. right arm) or an undiseased portion of the same organ or tissue, or other undiseased tissue. ELFAC activity between the reference electrode and each of the measurement electrodes 16 and treated similarly as described above for screening.

In order to determine whether and when noise is minimized and therefore diagnostically. useful ELFAC signals are obtained from a given subject, monitoring of these signals must be continuous from the time the last electrode is placed on the subject until representative ELFAC signals are obtained. It is well recognized that noise is produced at the skin/electrode interface due to the electrically resistive characteristics of the skin's stratum corneum. For skin surface electrodes to be effective transducers of electromagnetic fields generated by subsurface organ systems, the corneal barrier must be breeched. However, using even the most highly conductive electrode pastes and gels, achieving signal equilibration takes time; several minutes or even longer for a given subject. But more problematic is the fact that equilibration time can vary substantially on an individual basis and can even vary within an individual at different times and/or test site locations. This is because skin resistance and other factors related to transdermal activity vary on an individual basis. Previously the timing and duration of electromagnetic field measurement was predetermined and the same for each subject essentially built into the machine. This could lead to diagnostic errors because some subjects could be measured before equilibration was complete. In these cases, it was noise rather than signal which was measured and analyzed. The present invention circumvents this problem by continuous measurement and monitoring of ELFAC activity. This is accomplished by analyzing each incoming signal for stability on an individual basis. For example, the typical manifestation of uncompleted signal equilibration is a progressively decreasing (but not increasing) electrical potential seen soon after a measurement electrode is applied and the corneal layer is in the process of being penetrated by the electroconductive paste or gel. Eventually, once equilibration is complete, the informative signal of slowly rising and falling ELFAC potentials may be observed. In some embodiments, the present invention will not start recording and analyzing electromagnetic signals until the pattern recognition software in central processing unit 22 identifies the characteristic ELFAC waveforms which indicate that equilibration has taken place. This means that recording time and duration are not preset and the same for each subject, but that recording and analysis of electromagnetic activity will not take place until signal-to-noise is maximized for each subject tested. Each patient and each procedure therefore is assessed individually and independently to achieve noise-minimized data in each test in each patient. In some embodiments, the signals obtained during equilibration may be recorded, but not used in the screening or diagnostic analysis.

As described above, once noise-minimized ELFAC signals are identified, they are recorded and held in RAM memory 26 for analysis. The preprogrammed analysis software then employs nonlinear pattern recognition techniques of known types such as artificial neural networks or classification decision trees (e.g., CART). Specifically, all recorded voltages within the predetermined frequency range are fed into the pattern recognition program along with optional subject variables such as patient age, lesion size, family history of breast cancer (or disease being screened for, results of imaging studies, etc. The present invention contemplates that different pattern recognition programs will be employed for subsets of subjects based on these and other key variables. For example, the biological activity of malignant breast tumors may be different in premenopausal women as opposed to postmenopausal women because of differences in the hormonal milieu in some embodiments, these differences can be taken into account in the analysis. Small breast cancers which are non-palpable may be more metabolically active than larger tumors, whose central core often becomes necrotic. Likewise, metabolic activity of skin lesions may be tied to physical appearance, with those lesions appearing as darker, raised mole-like structures more likely to be highly metabolically active.

Figure 3:
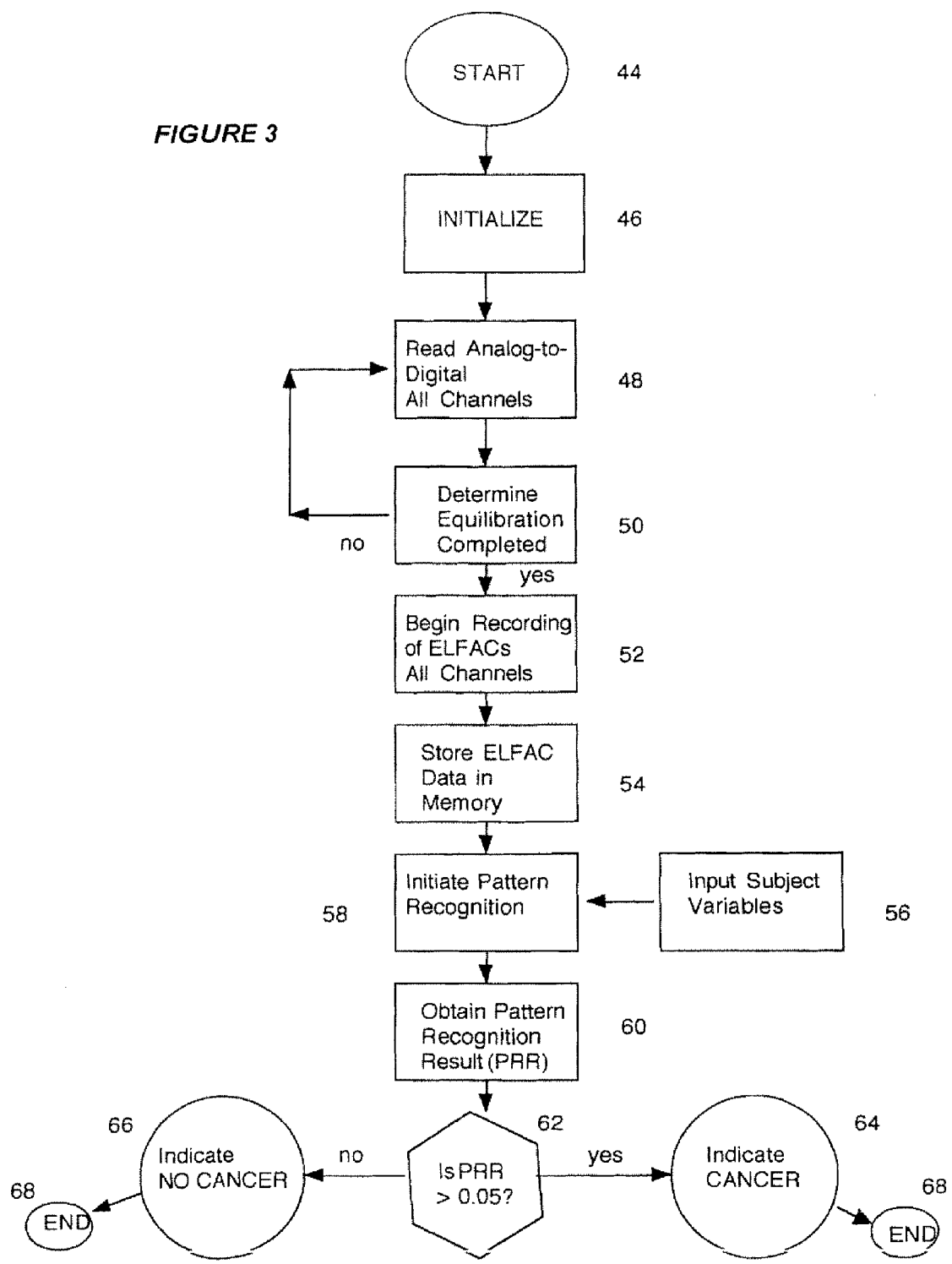
FIG. 3 is a flow diagram of the measurement operation of the apparatus of FIG. 1 used to obtain noise-minimized ELFAC signals.

The flow diagram in FIG. 3 provides an example of inputs, central processing, and the output of a pattern recognition program for the diagnosis of a skin lesion. A start switch 44 begins operation of the central processing unit 22, initializing processing operations 46. The initializing process brings the various components of the device 10 into operational mode, including resetting and activation of control registers to read data 48 from the analog-to-digital converters 20. As opposed to prior art devices, the current invention does not initiate a predetermined multiple measurement period at 48. Instead, data is read continuously until equilibration is completed at 50 and diagnostically useful ELFACs for each recording channel is identified. The continuous assessment of data at 50 is recycled back through step 48 until all or most of the channels are determined to carry noise-minimized ELFAC signals.

Figure 5:
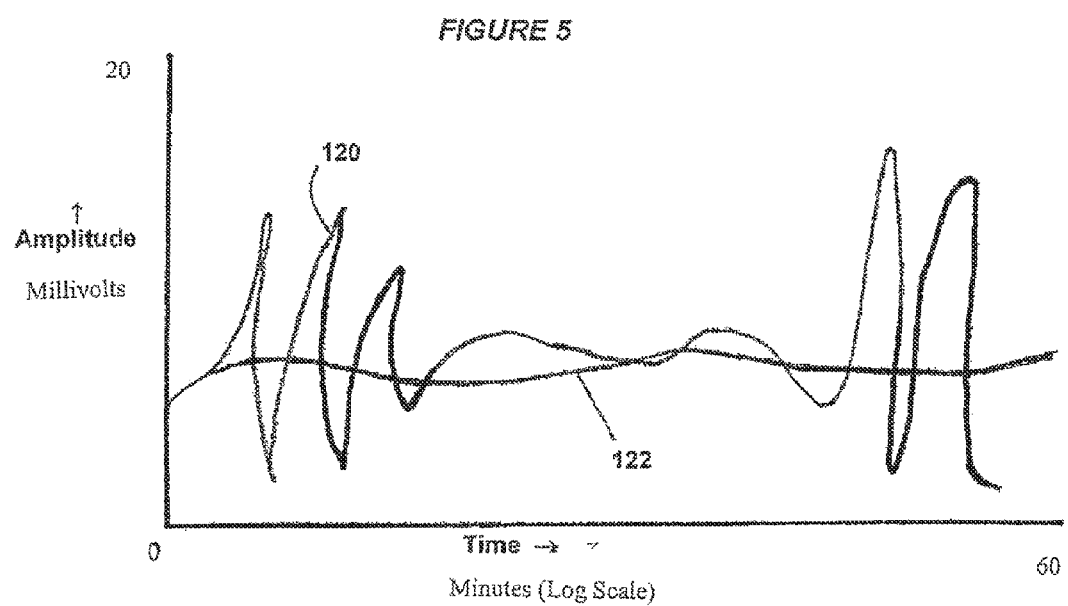
FIG. 5 is a diagram showing the differentiation between spurious electromagnetic activity due to skin/electrode equilibration and noise-minimized ELFAC signals.

FIG. 5 represents electromagnetic data as a function of time and amplitude. ELFAC signals digitized at 48 are determined at 50 to be either obscured by noise 112 or to have reached a noise minimized state 114. Only signals which have reached a noise minimized state 114 are recorded (saved) at 52 and stored for processing at 54.

Should a significant number of channels be determined as unable to transmit noise-minimized ELFAC signals within a reasonable amount of time (e.g., approximately 15 minutes) the operation would shut down and the central processing unit 22 would transmit instructions via output display device 28 for the medical technician to check contact points or employ other trouble shooting methods. In the case that some channels are unable to transmit noise-minimize ELFAC signals, the channels that are able to transmit such signals will be used, provided that the number of non-transmitting channels is not significant. That is to say that if substantially all the channels are transmitting, the transmitting channels will be used. By "substantially all" it is meant that at least 90% of all channels are able to transmit noise-minimized ELFAC signals.

Once noise-minimized ELFAC signals have been identified, they are captured and stored in memory 54. This is in contrast to prior art devices in which only the averaged DC component is stored in memory for processing. The pattern recognition module 58 incorporates nonlinear pattern recognition programs of known type such as artificial neural networks or decision trees which integrate ELFAC data and patient variables 56 such as patient age, lesion size or shape, level of suspicion from imaging studies, etc. to obtain a pattern recognition result 60 which leads to a probability statement 62 of whether a suspicious lesion is malignant (as used in a diagnostic mode) or whether an organ system may harbor an occult malignancy (as used in a screening mode). The resultant probability statement can be used to indicate CANCER at 64 if it exceeds a certain value, such as 0.05 (5%) or NO CANCER if it does not exceed this value, as in FIG. 4 at 66. This indication, or the underlying probability or other interpretation, can be output to a display device such as a monitor or printer and/or stored in memory. If the present invention is utilized in diagnostic mode, the probability cut-off point for indicating cancer can be reduced to minimize false negative results (i.e., missed cancers) in symptomatic populations with a high a priori prevalence of disease. If, on the other hand, the present invention is utilized in a screening setting, in which the a priori prevalence of disease is relatively low, the process at 76 could be calibrated to indicate cancer at a higher probability cut-off point. Depending on the specific application, the output to the user at 64 or 66 could, in addition to indicating CANCER or NO CANCER, also indicate the probability or likelihood that the diagnosis is correct, or a scalar output indicating disease severity. Once the output 64 or 66 is produced, the program terminates at 68.

Figure 4:
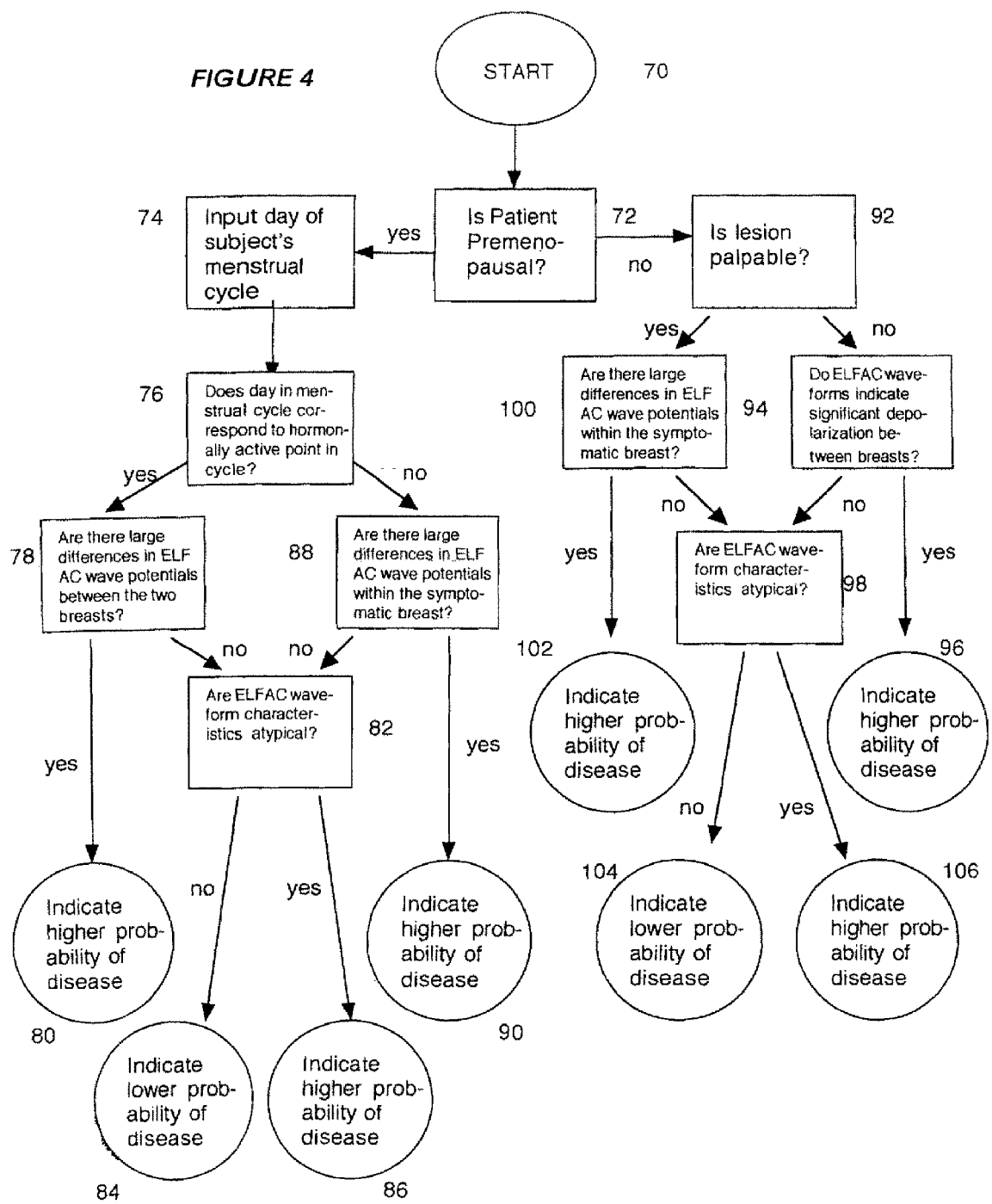
FIG. 4 is a flow diagram representing inputs and outputs of the disease decision pattern recognition program.

An example of a configuration of a pattern recognition module at 58 is given in FIG. 4. The pattern recognition program initiates at 70. Subject clinical information, inputted via standard devices at 56 such as a keypad or from a menu on a touch sensitive screen or any suitable input device, constitute the initial steps in the sequence. For example, at 72 the program diverges depending on whether the subject is pre- or post menopausal, if the subject is premenopausal, then the numerical value corresponding to day in menstrual cycle is entered at 74. The program diverges again at 76 if the subject is in a hormonally active segment of the menstrual cycle. This is because disease states are known to be influenced by systemic hormonal changes. If the subject is in a hormonally active segment, then the pattern recognition program might weight more heavily differences in point to point ELFAC potentials between the two mirror-image organ systems or locations 78, such as between two extremities or between two breasts. If significant differences are found at 78, then the PRR value 60 would indicate a higher probability of cancer, while if these differences are not observed then waveform characteristics 80 such as frequency, electrical potential at peak and/or trough of the ELFAC wave are examined to determine the probability outcome at 82 or 84. If on the other hand the patient is not in a hormonally active segment of the menstrual cycle, then maximum differences from electrode sites near the area of the symptoms (e.g., on the same breast or extremity) may be more heavily weighted by the pattern recognition program at 86. The program may then proceed to the output probability at 88 if a positive response is achieved, or proceed to 80 for waveform evaluation and subsequent probability output. The pattern recognition values may differ depending on whether the input comes from 78 or 86.

Moving now back to 72 in FIG. 4, if the patient is not premenopausal, then it is irrelevant to enter a value corresponding to day in menstrual cycle, as at 74. For the purposes of illustration, the data flow could proceed on the basis of whether the suspicious lesion being tested is palpable or not at 92. If more precise size information from imaging studies is available, these data could also be used. If the lesion is non-palpable, then the program may proceed to determine if the ELFAC waves indicate general depolarization in the area of the suspicious lesion (relative to measurements taken from the opposite breast or extremity) at 94 with eventual probability outputs at 96, or 104 or 106 via 98. If on the other hand the lesion is palpable at 92, then the pattern recognition program at 100 would weight maximum ELFAC differences from electrode sites near the area of the symptoms (e.g., on the same breast or extremity) rather than weighting overall depolarization relative to the opposite breast or extremity.

If ELFAC differences are above a preset threshold as determined by the preprogrammed algorithm at 98, then a higher probability of disease is indicated at 106. In each case at 94 and 100, negative outcomes would lead to waveform characteristic analysis at 98 with negative outcomes leading to statements of lower probability of disease at 104 and positive outcomes leading to statements of higher probability of disease at 106.

Although FIG. 4 provides one embodiment of a pattern recognition flowchart, the present invention also contemplates that other biological variables could be added to the pattern recognition module 58. For example, lesion palpability 92 could be integrated into the decision sequence for premenopausal subjects as well. In addition, the probability statements at 80, 84, 86, 90, 96, 102, 104, and 106 could be integrated with level of suspicion indexes from other diagnostic studies or previous ELFAC tests. The number and types of variables would depend on the specific application of disease diagnosis or screening. For example, a disease screening pattern recognition module would not include lesion characteristics such as palpability or size 92 in FIG. 4. Instead, there would be greater reliance placed on demographic variables such as subject age or family history of the disease state being screened.

Thus, different decision cut-off points or submodules (e.g., neural nets, decision trees) such as 78, 82, 88, 94, 98, and 100 in FIG. 4 are required for different biological situations in order maximize the effectiveness of utilizing electromagnetic fields for disease diagnosis and screening.

The method and apparatus of the present invention is designed to provide greater accuracy in diagnosing and screening for disease states using biologically tuned pattern recognition of extremely low frequency alternating current (ELFAC) signals. The signals are measured from a number of different sites on the body involving a known or suspicious disease site. Comparison of the informative aspects of the signals from the different sites such as periodicity, peaks, troughs, slopes and other information are integrated with subject variables to provide a greater accuracy in detecting and diagnosing disease states such as epithelial malignancies.

What is claimed is:

1. A method of screening for or diagnosing a disease condition in a test subject comprising:
    passively obtaining electromagnetic frequency signals, as a measure of native electropotentials of the test subject, between a test site and a reference site via at least one sensor electrode and at least one reference electrode;
    band pass filtering the signals obtained by the sensor electrode to yield sensor extremely low frequency alternating current (ELFAC) signals within a frequency range of 0.001 Hz to 0.1 Hz;
    bandpass filtering the signals obtained by the reference electrode to yield reference ELFAC signals;
    determining likelihood of disease based upon said ELFAC signals.

2. The method of claim 1, wherein said ELFAC signals are sent to a processing unit for use in the determining step, and wherein said processing unit outputs a determined result to a display device.

3. The method of claim 1, wherein said determining step comprises comparing one or more ELFAC field waveform measurements selected from periodicity, frequency, peaks, troughs, slopes, fractal dimensions, and chaos.

4. The method of claim 3, wherein said comparing step further comprises:
    correlating similar sensor and reference data with a low risk of disease state; and
    correlating dissimilar sensor and reference data with a higher risk of disease state.

5. The method of claim 1, wherein the reference electrode is placed on the test subject at a location complimentary or symmetrical to said test site.

6. The method of claim 1 wherein the reference electrode contacts a reference standard solution.

7. The method of claim 1 wherein said determining step uses the noise-minimized ELFAC data, wherein the equilibration period comprises establishing a noise-minimized status by continuously measuring ELFAC waveforms at said sensor electrode and said reference electrode during an equilibration period, wherein said equilibration period ends, and noise-minimized ELFAC data is achieved when substantially all of the measured ELFAC waveforms reach equilibrium.

8. The method of claim 3 whereby the comparing step is not performed unless and until noise-minimized ELFAC data has been achieved.

9. The method of claim 7 wherein noise-minimized ELFAC data are integrated with user input biological subject variables and compared using pattern recognition techniques, and a probability of a presence of a disease state is determined as a result of the pattern recognition.

10. The method of claim 9, wherein said biological subject variables are selected from age of the subject, menopausal stage, day in a menstrual cycle, palpability of a suspicious lesion, size of a suspicious lesion, dimensions of a suspicious lesion, and combinations thereof.

11. The method of claim 9 in which the biological subject variable is the menopausal stage of the subject from which the pattern recognition technique and waveform values to be employed for a given subject are determined.

12. The method of claim 9 in which the biological subject variable is the day in the menstrual cycle of the subject from which the pattern recognition technique and waveform values to be employed for a given subject are determined.

13. The method of claim 9 in which the biological subject variable is the palpability of a suspicious lesion from which the pattern recognition technique and waveform values to be employed for a given subject is determined.

14. The method of claim 9 in which the size or dimensions of a suspicious lesion determines the pattern recognition technique and waveform values to be employed for a given subject.

15. The method of claim 9 in which the age of the subject determines the pattern recognition technique and waveform values to be employed for a given subject.

16. The method of claim 9 which includes detecting and analyzing ELFAC waveform data in said subject between at least one location remote from the test site and said reference site and comparing a relationship between a remote measurement site ELFAC data and ELFAC data measured from at least one sensor electrode located at the test site, which includes determining a presence or absence of a disease state by comparison of said ELFAC data.

17. The method of claim 16 wherein said sensor electrode(s) at remote location on the subject is spaced away from the test site.

18. The method of claim 1 whereby electropotential measurements are taken sequentially from one or more locations on or in the body of a test subject.

19. The method of claim 1 whereby electropotential measurements are taken simultaneously or concurrently from one or more locations on or in the body of a subject human or animal.

20. The method of claim 7,
    wherein each sensor electrode is associated with a reference electrode, and the method further comprises
    grouping ELFAC signals for each association of sensor electrode and reference electrode;
    calculating a measure of central tendency of said signals taken from noise-minimized ELFAC measurements;
    comparing said measure of central tendency for the purpose of disease diagnosis and screening.

21. The method of claim 1, wherein at least one of the sensor electrode and the reference electrode are fixed to a patient's skin surface, which comprises the stratum corneum, the method further comprising removing of the stratum corneum at at least one of said test site and said reference site by concentrating a laser light on a dye layer placed on the skin surface to facilitate contact of at least one of the sensor electrode and the reference electrode.

22. An apparatus for disease detection or diagnosis at a test site on or in a test subject, said apparatus comprising:
    at least one sensor electrode designed for contact with the test site;
    at least one reference electrode for contact with a reference site;
    wherein said sensor electrode and said reference electrode passively obtain electromagnetic frequency signals, as a measure of native electropotentials of the test subject;
    a bandpass filter allowing passage of extremely low frequency alternating currents (ELFACs) within a frequency range of 0.001 Hz to 0.1 Hz;
    a processing means, configured to collect, analyze and store data obtained from the electrodes;
    wherein said sensor electrode and said reference electrode are operatively coupled to the processing means via the band pass filter.

23. The apparatus of claim 22 whereby the reference electrodes are of the same type as the sensing electrodes and placed at a location away from the test site on or in the test subject.

24. The apparatus of claim 22 whereby the reference electrodes are in contact with a solution of normal saline or other artificial reference material.

25. The apparatus of claim 22, further comprising
analog-to-digital converter component connected to receive the ELFAC signal from each said sensor electrode and said reference electrode to produce a digital signal and
wherein said processing means is connected to receive each said digital signal, said processing means operating to compare said digital ELFAC signals to yield a disease diagnosis or probability indicator.

26. The apparatus of claim 22, wherein at least one of said sensor electrodes or said reference electrodes comprises
an adhesive outer portion which affixes the electrode to a surface of the test or reference site,
an inner portion further comprising one or more micro-or mini-electrodes of a length capable of penetrating a corneal layer of the skin or outer layer of an organ system at the test site, and
wherein each micro-or mini-electrode is operatively coupled to the processing means.

27. The apparatus of claim 22, wherein said processing means comprises an equilibration module wherein each ELFAC signal is analyzed for equilibrium, such that only once equilibrium is reached, does the process perform further analyses.

28. The apparatus of claim 22, wherein said processing means comprises a pattern recognition module, wherein the data captured by the sensor electrode is compared to the data captured by the reference electrode, and correlated to the likelihood of a disease state being present.

* * * * *